(12) United States Patent
Cheng et al.

(10) Patent No.: US 11,357,888 B2
(45) Date of Patent: Jun. 14, 2022

(54) NANO-LAYERED DUAL HYDROXIDE-BIOLOGICAL FACTOR COMBINED SYSTEM FOR PROMOTING NERVE REGENERATION TO REPAIR SPINAL CORD INJURY

(71) Applicant: Shanghai Tongji Hospital, Putuo District Shanghai (CN)

(72) Inventors: Liming Cheng, Shanghai (CN); Shilong Wang, Shanghai (CN); Rongrong Zhu, Shanghai (CN)

(73) Assignee: Shanghai Tongji Hospital, Putuo District Shanghai (CN)

( * ) Notice: Subject to any disclaimer, the term of this patent is extended or adjusted under 35 U.S.C. 154(b) by 292 days.

(21) Appl. No.: 16/625,808

(22) PCT Filed: Oct. 23, 2018

(86) PCT No.: PCT/CN2018/111445
§ 371 (c)(1),
(2) Date: Dec. 23, 2019

(87) PCT Pub. No.: WO2019/153792
PCT Pub. Date: Aug. 15, 2019

(65) Prior Publication Data
US 2021/0154362 A1    May 27, 2021

(30) Foreign Application Priority Data

Feb. 8, 2018  (CN) .......................... 201810126426.X

(51) Int. Cl.
*A61L 27/22* (2006.01)
*A61L 27/04* (2006.01)
*A61L 27/54* (2006.01)

(52) U.S. Cl.
CPC .......... *A61L 27/227* (2013.01); *A61L 27/042* (2013.01); *A61L 27/047* (2013.01); *A61L 27/54* (2013.01); *A61L 2300/414* (2013.01); *A61L 2400/12* (2013.01); *A61L 2430/32* (2013.01); *A61L 2430/38* (2013.01)

(58) Field of Classification Search
None
See application file for complete search history.

(56) References Cited

U.S. PATENT DOCUMENTS

| 8,579,947 B2 | 11/2013 | Wu | |
|---|---|---|---|
| 2006/0136068 A1* | 6/2006 | de Bruijn | A61L 27/12 623/23.63 |
| 2011/0165218 A1 | 7/2011 | Cool et al. | |
| 2015/0321168 A1 | 11/2015 | Na et al. | |

FOREIGN PATENT DOCUMENTS

| CN | 103966160 A | 8/2014 |
|---|---|---|
| CN | 105999262 A | 10/2016 |
| CN | 108339151 A | 7/2018 |

OTHER PUBLICATIONS

Choy et al., "Layered double hydroxide as an efficient drug reservoir for folate derivatives", 2004, Biomaterials, vol. 25, pp. 3059-3064.*
Ladewig et al., "Efficient siRNA delivery to mammalian cells using layered double hydroxide nanoparticles", 2010, Biomaterials, vol. 31, pp. 1821-1829.*

* cited by examiner

*Primary Examiner* — Robert A Wax
*Assistant Examiner* — Randeep Singh
(74) *Attorney, Agent, or Firm* — Banner & Witcoff, Ltd.

(57) ABSTRACT

Disclosed is a nano-layered dual hydroxide-biological factor combined system for promoting nerve regeneration to repair a spinal cord injury. The preparation method therefor comprises: 1) synthesizing a nano-layered dual hydroxide CL1; and 2) co-incubating 10 mg CL1 and 200-2000 ng of biological factors NT3, VEGF or bFGF in a low-speed shaker at 4° C. for 2 hours using an ion exchange method, centrifuging same and then obtaining the precipitate. Experiments on transection and resorption spinal cord injury models show that this combined system has a significant recovery effect on the behavior of model mice, can reconstruct the neural circuit of a damaged area over time and achieves an ideal repair effect with regard to a spinal cord injury.

7 Claims, 4 Drawing Sheets

Figure 1:
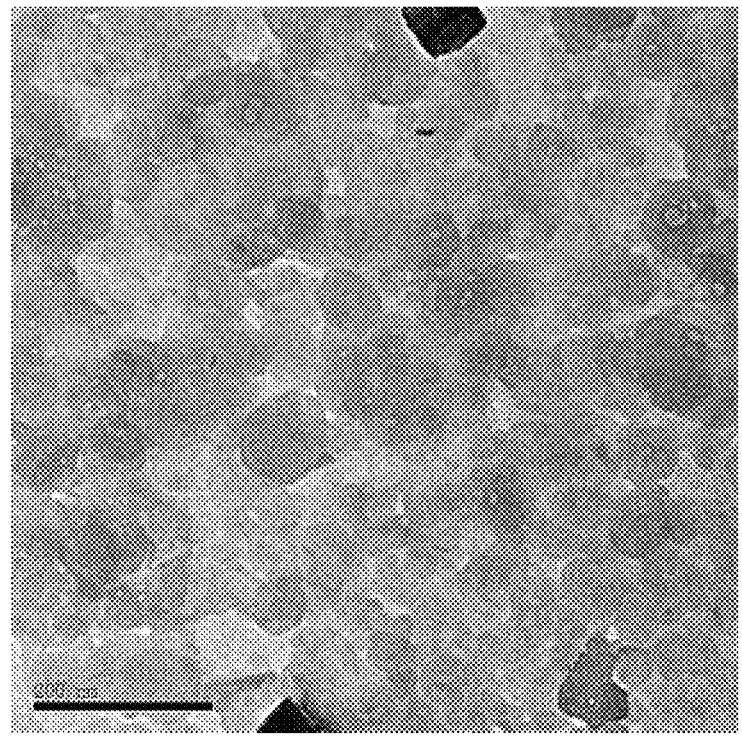

NANO-LAYERED DUAL HYDROXIDE-BIOLOGICAL FACTOR COMBINED SYSTEM FOR PROMOTING NERVE REGENERATION TO REPAIR SPINAL CORD INJURY

RELATED APPLICATIONS

This application is a National Stage Application under 35 U.S.C. 371 of co-pending PCT application PCT/CN2018/111445 designating the United States and filed Oct. 23, 2018; which claims the benefit of CN application number 201810126426.X and filed Feb. 8, 2018 each of which are hereby incorporated by reference in their entireties.

TECHNICAL FIELD OF THE INVENTION

The present invention refers to the field of biomedical technology, particularly to a nano-layered double hydroxide-biological factor combined material for promoting nerve regeneration to repair spinal cord injury, the preparation method thereof and use in the preparation of materials for the treatment of nerve injury or spinal cord injury thereof.

BACKGROUND OF THE INVENTION

Spinal cord injury (SCI), a difficult medical problem to date, has a high incidence, high disability rate, high cost and lower age in the world. Patients with spinal cord injury are mainly young and middle-aged, and the high-incidence age group is concentrated in 18-32 years old. The labor ability is almost completely lost, and severe disability is often caused after spinal cord injury. According to statistics, the incidence of spinal cord injury in China is 18-60 persons/million person/year, and there are more than 2 million patients with traumatic spinal cord injury, adding 0.1-0.14 million patients every year. The cost of rehabilitation for patients with spinal cord injury is high, causing a huge burden on families and society. The cost of patients with spinal cord injury in the United States is more than 6 billion dollars per year, and that in China is more than tens of billions of RMB per year.

At present, the treatment of spinal cord injury is mainly the clinical comprehensive treatment of surgical repair, neurotrophic therapy, hyperbaric oxygen therapy and modern rehabilitation intervention, but the ideal effect has not been achieved. The main reason is that the key problem how to effectively regenerate nerves and reconstruct neural circuits has not been solved fundamentally. In recent years, research progress in the fields of factor regulation and tissue engineering materials has provided important technical support for the regeneration and repair of spinal cord injury.

A variety of functional materials are currently being applied to the repair of spinal cord injury. In 2002, Kellerth et al of Umeå University in Sweden first used polyhydroxybutyrate (PHB) combined with alginate and fibrin as a scaffold to treat spinal cord injury in mice, and found that the scaffold reduced the number of neuronal deaths after spinal cord injury. Since then, there have been many scholars to carry out researches on the three-dimensional structure and biocompatibility microenvironment of bionic scaffolds to meet the needs of neural circuit reconstruction after spinal cord injury. In 2011, Ferreira et al of Coimbra University in Portugal reported that the nanomaterial polyethyleneimine loaded with retinoic acid promoted the differentiation of neural stem cells from subventricular zone into neurons. In 2013, Schaffer et al of the University of California, Berkeley, conjugated the extracellular domain of ephrin-B2 with hyaluronic acid to form multivalent coordination and found that the prepared nanomaterial induced signal transduction in neural stem cells and differentiation of stem cells into neurons. At present, there are many patents about scaffold materials for stem cell culture at home and abroad, such as patents of chitosan scaffolds (US20110093020; U.S. Pat. No. 9,180,166) and patents of collagen scaffolds (U.S. Pat. Nos. 9,205,106, 8,828,433). The above achievements indicate that the optimization and design of nanomaterials suitable for endogenous neural stem cell proliferation, differentiation and migration to construct the microenvironment needed to promote neural circuit reconstruction have great value in the research of spinal cord injury repair and prospect for clinical application.

Layered double hydroxide (LDH) is a kind of typical inorganic layered material. It is a hydroxide with a layered crystal structure composed of two or more metal ions. The layer structure is positively charged, and there are exchangeable anions between the layers. The delaminated nanosheet of layered double hydroxide has a positive charge and an opened structure of two-dimensional nanometer scale, and can be used as a novel element to assemble a functional composite nanostructure or material. So it is a kind of inorganic material having a wide range of uses. The inorganic material nanosheet has a large specific surface area and good dispersibility. The ultra-thin thickness of the nanosheet in the nanometer scale and the controllability of the layer ions make it have a wide range of applications in the fields of catalysis, emulsion stabilization and biology.

Chinese Patent Application No. 2014101424699 provides an application of inorganic nanomaterial layered double hydroxide in mouse embryonic stem cell culture. It disclosed that, without LIF, the nano-layered double hydroxide promoted various pluripotency genes expression and inhibited cell differentiation, and the treated cells still had the potential to differentiate into all cell type of three embryonic germ layers.

Chinese Patent Application No. 201410485883X provides a dexamethasone sodium phosphate-layered double hydroxide, the application for treating asthma thereof and preparation method thereof. The layered double hydroxide was used to mount dexamethasone sodium phosphate to improve the therapeutic effect and reduce the side effects of dexamethasone sodium phosphate. The dexamethasone sodium phosphate-layered double hydroxide had a high drug loading and a certain sustained release effect, and inhibited airway inflammation induced by egg protein in asthmatic rats, thus is expected to be applied to the treatment of asthma diseases.

Chinese Patent Application No. 2010105286223 provides a biological material for repairing spinal cord injury and the preparation method thereof, comprising the following steps: a) covalently crosslinking the ordered collagen material with 151 IgG to form an ordered collagen material that crosslinks 151 IgG, b) co-incubating the brain-derived neurotrophic factor containing the collagen binding region with the ordered collagen that crosslinks 151 IgG obtained in step a) to obtain the biomaterial for spinal cord injury repair. However, there have been no reports of spinal cord injury repair by means of nano-layered double hydroxide in the prior art.

Numerous studies have found that the proliferation, differentiation and survival of spinal cord neurons are affected by many specific protein molecules. For example, the ciliary neurotrophic factor (CNTF) produced by ciliary cells and astrocytes can promote the survival of injured and embryonic spinal cord neurons and has a great value in the treatment of human motor neuron degenerative diseases. In another example, glial cell line-derived neurotrophic factor (GDNF) can support the survival of midbrain dopaminergic neurons in vitro, also improve the survival rate of dopaminergic neurons and the density of nerve endings in various animal models of Parkinson's disease to improve their symptoms. In addition, protein molecules that promote neuronal growth include leukemia inhibitory factor (LIF), insulin like-growth factor-I (IGF-I), transforming growth factor (TGF), epidermal growth factor (EGF), fibroblast growth factor (FGF), platelet-derived growth factor (PDGF), and etc. There are some reports on the use of nano-layered double hydroxides to load small molecule drugs such as amoxicillin, however, there are few reports on the use of nano-layered double hydroxide to load biomacromolecules.

The particle size and morphology of the layered double hydroxide nanoparticles play a decisive role in its function and application. They are affected by the preparation method, the type and proportion of metal cations used, the type of embedded anions, the reaction temperature, the reaction time, and etc.

For the above reasons, it is unknown whether the factors that promote the growth of spinal cord neurons can be successfully loaded on a nano-layered double hydroxide to prepare a material with an ideal spinal cord injury repair effect in vivo.

SUMMARY OF THE INVENTION

The object of the present invention is to provide a nano-layered double hydroxide-biological factor combined material and a preparation method and use thereof in view of the deficiencies in the prior art.

In the first aspect, the present invention provides a use of nano-layered double hydroxide-biological factor combined material in preparing materials for promoting nerve regeneration and spinal cord injury repair, the preparation method of said nano-layered double hydroxide-biological factor combined material is as follows:

a) in order to synthesize nano-layered double hydroxide CL1, preparing CL1 nanoparticle suspension using $A(C)_2 \cdot 6H_2O$, $B(C)_3 \cdot 9H_2O$ and NaOH as raw materials and water as solvent, then obtaining soft gel by rotary centrifugation, the term "A" refers to a divalent ion, the term "B" refers to a trivalent ion, the term "C" refers to an anionic acid radical, b) to synthesize said nano-layered double hydroxide-biological factor combined material, based on ion exchange method, co-incubating 10 mg said CL1 and 200-2000 ng biological factor for 2 hours at 4 degrees on a low speed shaker, then collecting the precipitate after centrifugation to obtain said nano-layered double hydroxide-biological factor combined material, said biological factor is NT3, VEGF or bFGF.

In a preferred embodiment, the term "A" refers to a divalent ion, including, but not limited to, Mg, Ca, Cu and Zn.

In another preferred embodiment, the term "B" refers to a trivalent ion, including, but not limited to, Al, Fe and Cr.

In another preferred embodiment, the term "C" refers to an anionic acid radical, including, but not limited to, $NO_3^-$ and $CO_3^{2-}$.

In another preferred embodiment, the speed of said centrifugation is 5000-8500 rpm.

In another preferred embodiment, said biological factor is NT3.

In another preferred embodiment, the term "A" refers to Mg.

In another preferred embodiment, the term "B" refers to Fe.

In another preferred embodiment, the term "C" refers to $NO_3$.

In another preferred embodiment, said biological factor is NT3, the term "A" refers to Mg, the term "B" refers to Fe, and the term "C" refers to $NO_3$.

In the second aspect, the present invention provides a use of said nano-layered double hydroxide-biological factor combined material as described in any of the above in preparing materials for promoting behavioral recovery and electrophysiological recovery of spinal cord injury sites.

In the third aspect, the present invention provides a nano-layered double hydroxide-biological factor combined material that the preparation method of said nano-layered double hydroxide-biological factor combined material is as follows:

a) in order to synthesize nano-layered double hydroxide CL1, preparing CL1 nanoparticle suspension using $A(C)_2 \cdot 6H_2O$, $B(C)_3 \cdot 9H_2O$ and NaOH as raw materials and water as solvent, then obtaining soft gel by rotary centrifugation, the term "A" refers to a divalent ion, the term "B" refers to a trivalent ion, the term "C" refers to an anionic acid radical, b) to synthesize said nano-layered double hydroxide-biological factor combined material, based on ion exchange method, co-incubating 10 mg said CL1 and 200-2000 ng biological factor for 2 hours at 4 degrees on a low speed shaker, then collecting the precipitate after centrifugation to obtain said nano-layered double hydroxide-biological factor combined material, said biological factor is NT3, VEGF or bFGF.

In a preferred embodiment, the term "A" refers to a divalent ion, including, but not limited to, Mg, Ca, Cu and Zn.

In another preferred embodiment, the term "B" refers to a trivalent ion, including, but not limited to, Al, Fe and Cr.

In another preferred embodiment, the term "C" refers to an anionic acid radical, including, but not limited to, $NO_3$ and $CO_3^{2-}$.

In another preferred embodiment, said biological factor is NT3.

In another preferred embodiment, the term "A" refers to Mg.

In another preferred embodiment, the term "B" refers to Fe.

In another preferred embodiment, the term "C" refers to $NO_3$.

In another preferred embodiment, said biological factor is NT3, the term "A" refers to Mg, the term "B" refers to Fe, and the term "C" refers to $NO_3$.

In another preferred embodiment, the speed of said centrifugation is 5000-8500 rpm.

In the fourth aspect, the present invention provides a method of preparing nano-layered double hydroxide-biological factor combined material, comprising the following steps:

a) in order to synthesize nano-layered double hydroxide CL1, preparing CL1 nanoparticle suspension using $A(C)_2 \cdot 6H_2O$, $B(C)_3 \cdot 9H_2O$ and NaOH as raw materials and water as solvent, then obtaining soft gel by rotary centrifugation, the term "A" refers to a divalent ion, the term "B" refers to a trivalent ion, the term "C" refers to an anionic acid radical, b) to synthesize said nano-layered double hydroxide-biological factor combined material, based on ion exchange method, co-incubating 10 mg said CL1 and 200-2000 ng biological factor at 4 degrees for 2 hours on a low speed shaker, then collecting the precipitate after centrifugation to obtain said nano-layered double hydroxide-biological factor combined material, said biological factor is NT3, VEGF or bFGF.

In a preferred embodiment, the term "A" refers to a divalent ion, including, but not limited to, Mg, Ca, Cu and Zn.

In another preferred embodiment, the term "B" refers to a trivalent ion, including, but not limited to, Al, Fe and Cr.

In another preferred embodiment, the term "C" refers to an anionic acid radical, including, but not limited to, $NO_3$ and $CO_3^{2-}$.

In another preferred embodiment, said biological factor is NT3.

In another preferred embodiment, the term "A" refers to Mg.

In another preferred embodiment, the term "B" refers to Fe.

In another preferred embodiment, the term "C" refers to $NO_3$.

In another preferred embodiment, said biological factor is NT3, the term "A" refers to Mg, the term "B" refers to Fe, and the term "C" refers to $NO_3$.

In another preferred embodiment, the speed of said centrifugation is 5000-8500 rpm.

The advantages of this invention are as follows:

1) The present invention is the first attempt to use nano-layered double hydroxide as a filler for damaged sites to repair spinal cord injury, and this method is proved to be feasible.

2) The invention successfully synthesizes a nano-layered double hydroxide carrying a series of biological factors with good biocompatibility, good controlled release effect and optimized preparation parameters. It is confirmed that the material has a significant recovery effect on the behavior of mouse model of spinal cord transection. The material can reduce the inflammatory response in the spinal cord injury area, provide a good micro-environment for nerve regeneration, and achieve regeneration of endogenous neural stem cells and neurons. Electrophysiological signals are enhanced over time. The above evidences indicate that the material can reconstruct the neural circuit of the spinal cord injury area.

The treatment of spinal cord injury is a recognized medical problem in the world. At present, the comprehensive treatment through surgical repair and modern rehabilitation intervention has not achieved a desired effect. The fundamental reason is that the problem of nerve regeneration and neural circuit reconstruction after spinal cord injury has not been effectively solved. The present invention provides a whole new rehabilitation treatment strategy, which is helpful for the effective repair of spinal cord injury.

BRIEF DESCRIPTION OF THE DRAWINGS

FIG. 1 is a transmission electron micrograph of the nano-layered double hydroxide CL1.

FIG. 2 is a transmission electron micrograph of CL1-NT3 material.

FIG. 3 is a schematic illustration of filling the spinal cord transection sites with the CL1-NT3 material.

FIG. 4 is a graph showing the results of behavioral recovery of model mice after filling the spinal cord transection sites with CL1-NT3 material.

FIG. 5 is a graph showing the results of electrophysiological function recovery of model mice after filling the spinal cord transection sites with CL1-NT3 material.

DETAILED DESCRIPTION OF THE PREFERRED EMBODIMENT

The invention is further illustrated below in conjunction with specific embodiments. These examples are for illustrative purposes only and are not intended as limitations on the scope of the invention. In addition, changes therein and other uses will occur to those skilled in the art. Such changes and other uses can be made without departing from the scope of the invention as set forth in the claims.

As used herein, the term "preparing materials for improving nerve regeneration and spinal cord injury repair" refers to preparing a drug or medical device such as scaffold for improving nerve regeneration and spinal cord injury repair by using nano-layered double hydroxide-biological factor combined material as one of raw materials. Typically, said scaffold refers to a nerve scaffold that can be used alone for nerve regeneration and repair, or can be combined with cells or active factors for nerve regeneration and repair. Said nerve scaffold can be of various permissible shapes, such as a cylindrical shape, a rectangular parallelepiped, a quadrangular prism, and etc. In certain instances, the nerve scaffold has suitable strength, stiffness, and elasticity to provide a three-dimensional space required for nerve cell growth. In addition, said nerve scaffold may also have a degradable material with high strength and slow degradation rate on the outer layer to shield and prevent the growth of connective tissue, and have a degradable material suitable for cell growth in the inner layer. The degradable materials include, but are not limited to, polyglycolic acid (PGA), polylactic acid (PLA), copolymers thereof, polyacrylonitrile (PAN), polyvinyl chloride (PVC), and etc.

The use of the nano-layered double hydroxide-biological factor combined material includes treatment of any disease associated with repair of nerve injury or spinal cord injury. The nerve injury includes central nervous system injury and peripheral nerve injury. The nerve injury is caused by violence, mechanical compression, bleeding, electrolyte spillover or ischemic perfusion. In one embodiment, the nerve injury is central nerve injury, including spinal cord injury or brain injury, and the spinal cord injury is acute or chronic. The spinal cord injury is any type of injury in which the spinal cord, a part of the central nervous system, is damaged due to external or internal causes and thus does not perform its original function.

The spinal cord injury includes: traumatic spinal cord injury (dislocation or subluxation of the pyramidal joint), pyramidal fracture (linear fracture, compression fracture, contusion fracture, complete transverse injury, incomplete transverse injury, Brown-Sequard injury, acute anterior spinal cord injury, acute central spinal cord injury, high cervical spinal cord injury, etc.), spinal degenerative disease (spine joint rigidity, etc.), vertebral inflammatory disease (spondylitis, chronic rheumatoid arthritis, etc.), tumors (spinal cord tumors, spinal tumors, etc.), vascular diseases (spinal hemorrhage, spinal cord paralysis caused by extramedullary vascular disorders, etc.), myelitis (arachnoiditis, viral myelitis, bacterial myelitis, etc.), multiple sclerosing, amyotrophic lateral sclerosis, etc. Neuropathies caused by the spinal cord injury includes: lower body motor dysfunction, hemiplegia, lower body paralysis, sensory disturbance, autonomic dysfunction, loss of reflex, low sexual function, etc. The motor dysfunction caused by the neuropathies includes: shock based on neuropathy, respiratory paralysis, perceptual paralysis, motor paralysis, loss of reflex, autonomic nerve paralysis, etc. Additionally, it is to be understood that nano-layered double hydroxide-biological factor combined material of the present invention can be applied not only to the cure of diseases but also to the prevention, maintenance (prevention of deterioration), reduction (improvement of symptoms), and the like of diseases.

The methods and uses of the present invention are applicable to mammals including, but not limited to, vertebrates and rodents such as humans, mice, rats, rabbits, domestic animals, etc.

In the present invention, the dosage form and the dose to be administered can be appropriately selected depending on the nature and progress of the target disease, the administration method, etc. Preferably, the mode of administration is direct or post-dispersion injection.

As used herein, the term "the neurotrophin-3 (NT-3)" refers to a member of the nerve growth factor family. NT3 is widely distributed in the peripheral and central nervous system. It is a protein that has the functions of nourishing sensory neurons and motor neurons, and can regulate the growth, development, differentiation, regeneration and function of nerve cells. NT3 can maintain the survival of neurons, promote the differentiation and reproduction of neurons, increase the speed of sensory and motor conduction, promote the regeneration of peripheral nerves, prevent the axonal and motor endplate degeneration, and regulate the development of neuromuscular synapses. However, NT3 is unstable in vivo. It is easily diluted or degraded, and its absorption rate is not high. Thus, its efficacy in clinical application is low.

Vascular endothelial growth factor (VEGF), also known as vascular permeability factor (VPF), is a highly specific pro-vascular endothelial growth factor that promotes increase of vascular permeability, increase of extracellular matrix denaturation, migration and proliferation of vascular endothelial cell, angiogenesis, etc. The studies have shown that VEGF expression is up-regulated in a rat model with acute spinal cord injury, and VEGF has the function to protect nerve and repair spinal cord injury.

Basic fibroblast growth factor (bFGF) is a heparin-binding protein that promotes cell division and induces proliferation and differentiation of various cells, and plays an important role in the nervous system. bFGF is mainly distributed in pituitary, brain, nerve tissue, retina, adrenal gland, placenta, etc., and can be extracted and purified from various tissues derived from neuroectoderm and mesoderm (such as cerebral cortex, hypothalamus, pituitary, retina, etc.). The biological function of bFGF is extremely extensive. It is very important in angiogenesis, wound healing, tissue repair, tissue regeneration, and the growth and development of nerve tissue. As a neurotrophic factor, bFGF has been shown to be a mitogen of glial cells and schwann cells. It can prolong the survival time of various central and peripheral neurons in culture medium in vitro, stimulate the synthesis of choline acetylase and the growth of protrusions. When used in the brain for injury, it can promote the survival of hippocampal neurons, while the hippocampal nerves die without it. In the peripheral nervous system, when bFGF is added to the sciatic nerve cut, it can promote myelination of the nerve and prevent the death of dorsal root ganglion neurons.

The NT-3, VEGF and bFGF as used herein can be naturally occurring, such as they can be isolated or purified from the mammal. In addition, they can also be artificially prepared proteins, for example, recombinant proteins produced according to conventional genetic engineering recombination techniques. Preferably, the present invention uses recombinant proteins.

Any suitable proteins can be used in the present invention. These proteins include full length proteins or biologically active fragments thereof, and also include the amino acid sequence formed by substitution, deletion or addition of one or more amino acid residues. The full-length proteins or biologically active fragments thereof include the amino acid sequence obtained by substituting a conserved amino acid partial sequence and retaining all or part of the activity. Proper replacement of amino acids is a technique well known in the art that can be readily implemented and ensures that the biological activity of the resulting molecule is not altered. It is known to those skilled in the art that, in general, altering a single amino acid in a non-essential region of a polypeptide does not substantially alter biological activity of it. Such technique is described in Watson et al, Molecular Biology of The Gene, Fourth Edition, 1987, The Benjamin/Cummings Pub. Co. P224.

Bioactive fragments of any of the proteins can be used in the present invention.

The protein can also be a modified protein, such as a protein modified to in terms of half-life, effectiveness, metabolism, and/or protein potency. The said modified protein can be a protein conjugate, or it can comprise a substituted or artificial amino acid. The modified protein can have a small commonality with the naturally occurring protein, but can also form a complex with the layered double hydroxide to promote nerve regeneration and spinal cord injury repair in vivo without causing other defects and toxicity. That is, any protein modification technique that does not affect the biological activity of the protein can be used in the present invention.

The corresponding nucleotide coding sequence can be conveniently derived from the amino acid sequence of the protein. Those skilled in the art can construct expression vectors containing any of the above protein coding sequences and suitable transcription or translation control signal peptide expression sequences using well-known methods, including DNA recombination techniques in vitro, DNA synthesis techniques, DNA recombination techniques in vivo, and so on. In the expression vectors, the DNA sequence is operably linked to a suitable promoter to direct mRNA synthesis. The expression vectors also include a ribosome binding site for translation initiation and a transcription terminator. The expression vector can replicate and stably express any of the above proteins in a host.

In the following examples, NT3 was purchased from Peprotech and the product code was 450-03-100. VEGF was purchased from Peprotech and the product code was 450-32-50. bFGF was purchased from Peprotech and the product code was 450-33-50.

Example 1 Preparation of Nano-Layered Double Hydroxide CL1

The procedure of CL1 synthesis was performed as follows. A total of 40 ml of a mixed metal salt solution of $Mg(NO_3)_2 \cdot 6H_2O$ (1.536 g, 0.006 mol) and $Al(NO_3)_3 \cdot 9H_2O$ (0.75 g, 0.002 mol) was prepared, and water was used as a solvent, wherein the molar ratio of Mg to Al was 1:1. 0.016 mol NaOH solution was prepared. In a $N_2$ atmosphere, the mixed metal salt solution was added to the vigorously stirred NaOH solution, and the prepared suspension was transferred to a hydrothermal synthesis kettle, and removed after reacting at 100° C. for 18 h. Thereby, a CL1 nanoparticle suspension having a particle size of 20 to 200 nm was obtained. The synthesized CL1 was observed by transmission electron microscopy (FIG. 1) and presented a good hexagonal crystal structure, which is hexagonal. The synthesized CL1 nanoparticle suspension was placed in a centrifuge and centrifuged at 8500 rpm to form a soft gel.

Example 2 Preparation of Nano-Layered Double Hydroxide CL1

The procedure of CL1 synthesis was performed as follows. A total of 40 ml of a mixed metal salt solution of $Ca(NO_3)_2 \cdot 6H_2O$ (0.006 mol) and $Fe(NO_3)_3 \cdot 9H_2O$ (0.002 mol) was prepared, and water was used as a solvent, wherein the molar ratio of Ca to Fe was 1:1. 0.016 mol NaOH solution was prepared. In a $N_2$ atmosphere, the mixed metal salt solution was added to the vigorously stirred NaOH solution, and the prepared suspension was transferred to a hydrothermal synthesis kettle, and removed after reacting at 100° C. for 18 h. Thereby, a CL1 nanoparticle suspension having a particle size of 20 to 200 nm was obtained. The synthesized CL1 was observed by transmission electron microscopy and presented a good hexagonal crystal structure, which is hexagonal. The synthesized CL1 nanoparticle suspension was placed in a centrifuge and centrifuged at 8500 rpm to form a soft gel.

Example 3 Preparation of Nano-Layered Double Hydroxide CL1

The procedure of CL1 synthesis was performed as follows. A total of 40 ml of a mixed metal salt solution of $Cu(CO_3)_2 \cdot 6H_2O$ (0.006 mol) and $Cr(CO_3)_3 \cdot 9H_2O$ (0.002 mol) was prepared, and water was used as a solvent, wherein the molar ratio of Cu to Cr was 1:1. 0.016 mol NaOH solution was prepared. In a $N_2$ atmosphere, the mixed metal salt solution was added to the vigorously stirred NaOH solution, and the prepared suspension was transferred to a hydrothermal synthesis kettle, and removed after reacting at 100° C. for 18 h. Thereby, a CL1 nanoparticle suspension having a particle size of 20 to 200 nm was obtained. The synthesized CL1 was observed by transmission electron microscopy and presented a good hexagonal crystal structure, which is hexagonal. The synthesized CL1 nanoparticle suspension was placed in a centrifuge and centrifuged at 8500 rpm to form a soft gel.

Example 4 Preparation of Nano-Layered Double Hydroxide-NT3 Combined Material (CL1-NT3

The procedure of CL1 synthesis was performed as follows. A total of 40 ml of a mixed metal salt solution of $Mg(NO_3)_2 \cdot 6H_2O$ (1.536 g, 0.006 mol) and $Al(NO_3)_3 \cdot 9H_2O$ (0.75 g, 0.002 mol) was prepared, and water was used as a solvent, wherein the molar ratio of Mg to Al was 1:1. 0.016 mol NaOH solution was prepared. In a $N_2$ atmosphere, the mixed metal salt solution was added to the vigorously stirred NaOH solution, and the prepared suspension was transferred to a hydrothermal synthesis kettle, and removed after reacting at 100° C. for 18 h. Thereby, a CL1 nanoparticle suspension having a particle size of 20 to 200 nm was obtained. The synthesized CL1 was observed by transmission electron microscopy (FIG. 1) and presented a good hexagonal crystal structure, which is hexagonal. The synthesized CL1 nanoparticle suspension was placed in a centrifuge and centrifuged at 8500 rpm to form a soft gel.

Figure 2:
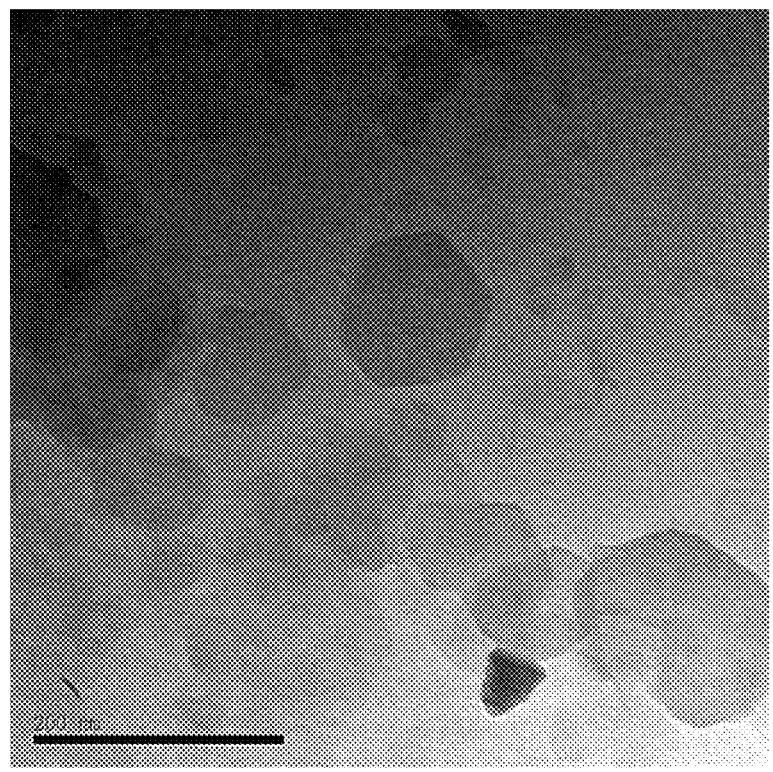

The procedure of nano-layered double hydroxide-biological factor combined material based on ion exchange method was performed as follows. Under the condition of 4 degrees, the nano-layered double hydroxide CL1 (dry weight 10 mg) and the neurotrophic factor NT3 (200-2000 ng) were co-incubated for 2 hours in a low-speed shaker, and after centrifugation, a precipitate was collected to obtain CL1-NT3. The synthesized CL1-NT3 was observed by transmission electron microscopy (FIG. 2).

Example 5 Preparation of Nano-Layered Double Hydroxide-VEGF Combined Material (CL1-VEGF The procedure of CL1 synthesis was performed as follows. A total of 40 ml of a mixed metal salt solution of $Mg(NO_3)_2 \cdot 6H_2O$ (1.536 g, 0.006 mol) and $Al(NO_3)_3 \cdot 9H_2O$ (0.75 g, 0.002 mol) was prepared, and water was used as a solvent, wherein the molar ratio of Mg to Al was 1:1. 0.016 mol NaOH solution was prepared. In a $N_2$ atmosphere, the mixed metal salt solution was added to the vigorously stirred NaOH solution, and the prepared suspension was transferred to a hydrothermal synthesis kettle, and removed after reacting at 100° C. for 18 h. Thereby, a CL1 nanoparticle suspension having a particle size of 20 to 200 nm was obtained. The synthesized CL1 was observed by transmission electron microscopy (FIG. 1) and presented a good hexagonal crystal structure, which is hexagonal. The synthesized CL1 nanoparticle suspension was placed in a centrifuge and centrifuged at 8500 rpm to form a soft gel.

The procedure of nano-layered double hydroxide-biological factor combined material based on ion exchange method was performed as follows. Under the condition of 4 degrees, CL1 (dry weight 10 mg) and VEGF (200-2000 ng) were co-incubated for 2 hours in a low-speed shaker, and after centrifugation, a precipitate was collected to obtain CL1-VEGF.

Example 6 Preparation of Nano-Layered Double Hydroxide-Multiple Factors Combined Material (CL1-VEGF-bFGF The procedure of CL1 synthesis was performed as follows. A total of 40 ml of a mixed metal salt solution of $Mg(NO_3)_2 \cdot 6H_2O$ (1.536 g, 0.006 mol) and $Al(NO_3)_3 \cdot 9H_2O$ (0.75 g, 0.002 mol) was prepared, and water was used as a solvent, wherein the molar ratio of Mg to Al was 1:1. 0.016 mol NaOH solution was prepared. In a $N_2$ atmosphere, the mixed metal salt solution was added to the vigorously stirred NaOH solution, and the prepared suspension was transferred to a hydrothermal synthesis kettle, and removed after reacting at 100° C. for 18 h. Thereby, a CL1 nanoparticle suspension having a particle size of 20 to 200 nm was obtained. The synthesized CL1 was observed by transmission electron microscopy (FIG. 1) and presented a good hexagonal crystal structure, which is hexagonal. The synthesized CL1 nanoparticle suspension was placed in a centrifuge and centrifuged at 8500 rpm to form a soft gel.

The procedure of nano-layered double hydroxide-biological factor combined material based on ion exchange method was performed as follows. Under the condition of 4 degrees, CL1 (dry weight 10 mg), VEGF and bFGF (the total amount of VEGF and bFGF is 200-2000 ng) were co-incubated for 2 hours on a low speed shaker, and after centrifugation, a precipitate was collected to obtain CL1-VEGF-bFGF.

Figure 3:
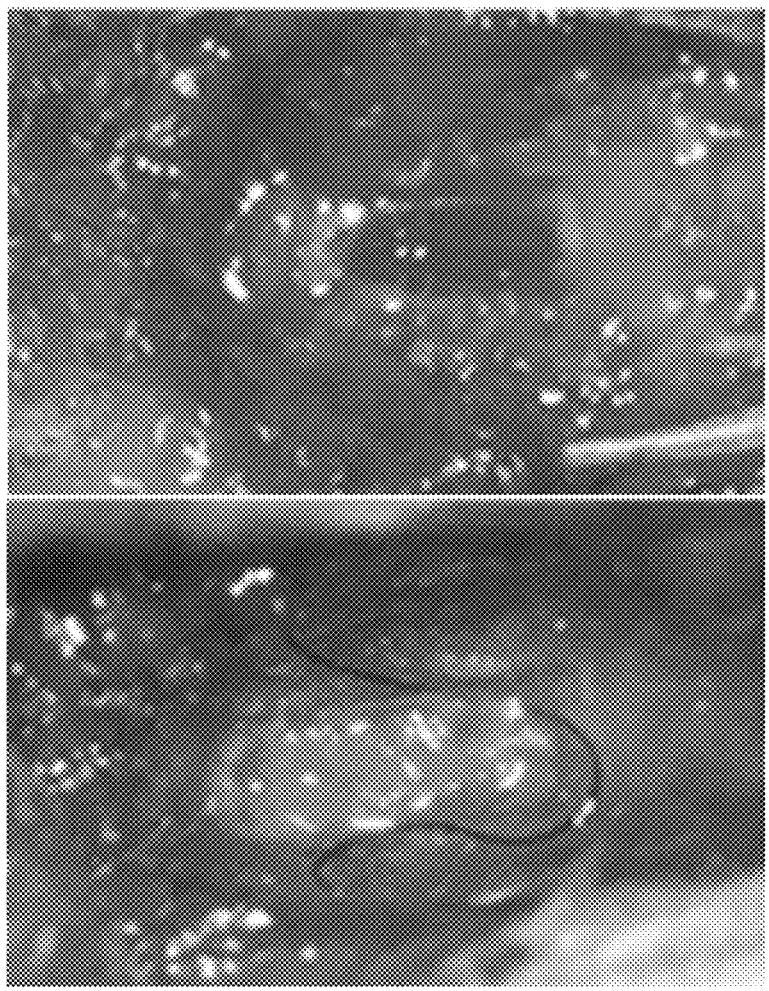

Example 7 Experiment of Nano-Layered Double Hydroxide-Factor Combined Material in Treating Spinal Cord Injury Animals The animals for experiment were model mice of 2 mm spinal cord transection. The specific method of making model can be found in the literature: Liu Rui, You Si, Liu Huiling, et al. Establishment of rat spinal cord transection injury model. Journal of Neuroanatomy. 2005, 21 (3): 263-268. As shown in FIG. 3, soft gelatinous CL1, CL1-NT3, CL1-VEGF or CL1-VEGF-bFGF was carefully filled into the spinal cord transection sites of the mice without squeezing to the surrounding spinal cord tissue. The mice were then routinely cared for. BMS score was evaluated weekly to evaluate the therapeutic effect of the material. BMS scoring method reference: Basso D M, et al. Basso Mouse Scale for locomotion detection differences in recovery after spinal cord injury in five common mouse strains. Journal of neurotrauma. 2006, 23(5): 635-659. Electrical stimulation was applied to the leg muscles of the mice with a stimulating electrode, and electrical stimulation was received with the receiving electrode at the head end and the tail end of the spinal cord transection site.

Figure 4:
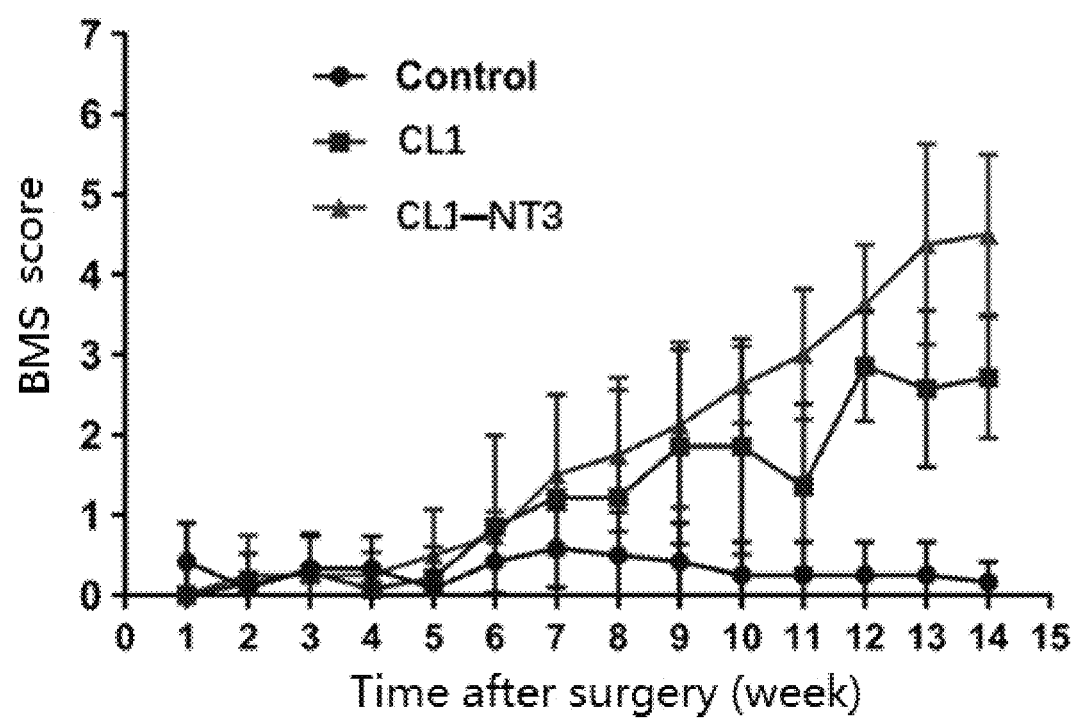

As shown in FIG. 4, each group of mice scored 0 points after spinal cord injury, and completely lost hind limb motor function. Next, the recovery of behavioral abilities of mice in each treatment group was promoted. From the 5th week, the recovery of hindlimb motor function in CL1 group and CL1-NT3 group showed a better trend than the control group. From the 6th week, the recovery of hindlimb motor function in CL1-NT3 group showed a better trend than CL1 group. At 13 weeks postoperatively, the CL1-NT3 group had the highest BMS score, and the highest score in the mouse scored 6 points (out of 9 points) with an average score of 4.5 points, while the control group scored only 0.5 to 1 point. In addition, the highest score of CL1-VEGF group was up to 3 points, and the highest score of CL1-VEGF-bFGF was up to 3 points, but the average score of CL1-VEGF-bFGF group was slightly higher than that of CL1-VEGF group. The above results indicate that the nanolayered double hydroxide-factor system of the present invention has a significant promoting effect on the behavioral recovery of model mouse of spinal cord transaction.

Figure 5:
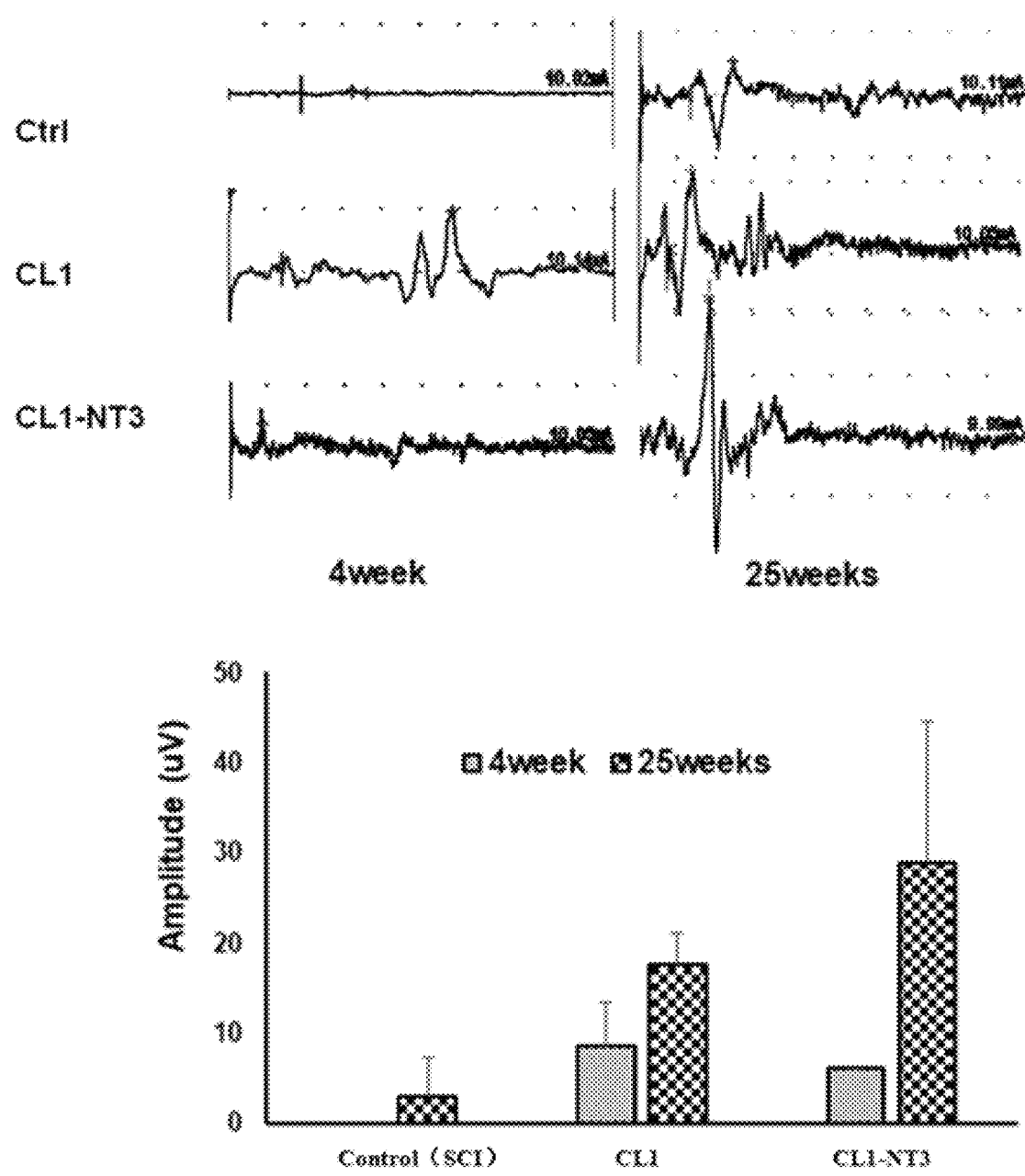

Further, electrical stimulation was applied to the leg muscles of the mouse by the stimulating electrode, and electrical stimulation was received with the receiving electrode at the head end and the tail end of the spinal cord transversely. The better the nerve conduction recovery of the spinal cord transection site, the more the electrical stimulation can be transmitted to the end of the transection site, that is, the electrical signal received by the receiving electrode at the head end has a larger amplitude value. As shown in FIG. 5, from the 4th week, the CL1 group and the CL1-NT3 group had higher amplitude values than the control group, and the CL1-NT3 group had the largest amplitude value. The above results indicate that nano-layered double hydroxide-biological factor combined material has a significant recovery effect on the electrophysiological function of the model mice, and the electrophysiological signal is enhanced over time, indicating that the neural circuit in the spinal cord injury area is reconstructed.

Example 8 Preparation of Nano-Layered Double Hydroxide CL1

The procedure of CL1 synthesis was performed as follows. A total of 40 ml of a mixed metal salt solution of $Zn(NO_3)_2 \cdot 6H_2O$ 0.006 mol) and $Cr(NO_3)_3 \cdot 9H_2O$ 0.002 mol) was prepared, and water was used as a solvent, wherein the molar ratio of Zn to Cr was 1:1. 0.016 mol NaOH solution was prepared. In a $N_2$ atmosphere, the mixed metal salt solution was added to the vigorously stirred NaOH solution, and the prepared suspension was transferred to a hydrothermal synthesis kettle, and removed after reacting at 100° C. for 18 h. Thereby, a CL1 nanoparticle suspension having a particle size of 20 to 200 nm was obtained. The synthesized CL1 was observed by transmission electron microscopy and presented a good hexagonal crystal structure, which is hexagonal. The synthesized CL1 nanoparticle suspension was placed in a centrifuge and centrifuged at 8500 rpm to form a soft gel.

Example 9 Preparation of Nano-Layered Double Hydroxide-Biological Factor Combined Material (CL1-VEGF A soft gel of nano-layered double hydroxide CL1 was prepared according to the method described in any of Examples 1-3.

The procedure of nano-layered double hydroxide-biological factor combined material based on ion exchange method was performed as follows. Under the condition of 4 degrees, CL1 (dry weight 10 mg) and VEGF (200-2000 ng) were co-incubated for 2 hours on a low speed shaker, and after centrifugation, a precipitate was collected to obtain CL1-VEGF. CL1-VEGF and CL1-VEGF-bFGF were prepared in the same method.

Example 10 Comparison Functions of Different Nano-Layered Double Hydroxide-Biological Factor Materials 1 Methods
1.1 Animal Grouping and Treatment The functions of different nano-layered double hydroxide-biological factor materials to repair the spinal cord injury were compared. A large number of experimental groups were set up and included:

Group 1: CL1 was prepared in substantially the same procedure as in Example 1, except that the molar ratio of Mg to Al was 2:1. Then, based on ion exchange method, CL1 (dry weight 10 mg) and NT3 (200 ng) were co-incubated for 2 hours under the condition of 4 degrees on a low speed shaker, and after centrifugation, a precipitate was collected to obtain CL1-NT3.

Group 2: CL1 was prepared in substantially the same procedure as in Example 1, except that the molar ratio of Mg to Al was 1:2. Then, based on ion exchange method, CL1 (dry weight 10 mg) and NT3 (200 ng) were co-incubated for 2 hours under the condition of 4 degrees on a low speed shaker, and after centrifugation, a precipitate was collected to obtain CL1-NT3.

Group 3: CL1 was prepared in substantially the same procedure as in Example 1, except that the molar ratio of Mg to Al was 1:3. Then, based on ion exchange method, CL1 (dry weight 10 mg) and NT3 (200 ng) were co-incubated for 2 hours under the condition of 4 degrees on a low speed shaker, and after centrifugation, a precipitate was collected to obtain CL1-NT3.

Group 4: CL1 was prepared in the same procedure as in Example 2. Then, based on ion exchange method, CL1 (dry weight 10 mg) and NT3 (200 ng) were co-incubated for 2 hours under the condition of 4 degrees on a low speed shaker, and after centrifugation, a precipitate was collected to obtain CL1-NT3.

Group 5: CL1 was prepared in substantially the same procedure as in Example 1, except that dilute aqueous ammonia was used instead of the NaOH solution. Then, based on ion exchange method, CL1 (dry weight 10 mg) and NT3 (200 ng) were co-incubated for 2 hours under the condition of 4 degrees on a low speed shaker, and after centrifugation, a precipitate was collected to obtain CL1-NT3.

Group 6: CL1 was prepared in the same procedure as in Example 1. Then, based on ion exchange method, CL1 (dry weight 10 mg) and NT3 (200 ng) were co-incubated for 2 hours under the condition of 0 degrees on a low speed shaker, and after centrifugation, a precipitate was collected to obtain CL1-NT3.

Group 7: CL1 was prepared in the same procedure as in Example 1. Then, based on ion exchange method, CL1 (dry weight 10 mg) and NT3 (200 ng) were co-incubated for 2 hours under the condition of 2 degrees on a low speed shaker, and after centrifugation, a precipitate was collected to obtain CL1-NT3.

Group 8: CL1 was prepared in the same procedure as in Example 1. Then, based on ion exchange method, CL1 (dry weight 10 mg) and NT3 (200 ng) were co-incubated for 2 hours under the condition of 4 degrees on a low speed shaker, and after centrifugation, a precipitate was collected to obtain CL1-NT3.

Group 9: CL1 was prepared in the same procedure as in Example 1. Then, based on ion exchange method, CL1 (dry weight 10 mg) and NT3 (200 ng) were co-incubated for 2 hours under the condition of 5 degrees on a low speed shaker, and after centrifugation, a precipitate was collected to obtain CL1-NT3.

Group 10: CL1 was prepared in the same procedure as in Example 1. Then, based on ion exchange method, CL1 (dry weight 10 mg) and NT3 (200 ng) were co-incubated for 2 hours under the condition of 20 degrees on a low speed shaker, and after centrifugation, a precipitate was collected to obtain CL1-NT3.

Group 11: CL1 was prepared in the same procedure as in Example 1. Then, based on ion exchange method, CL1 (dry weight 10 mg) and NT3 (200 ng) were co-incubated for 2 hours under the condition of 37 degrees on a low speed shaker, and after centrifugation, a precipitate was collected to obtain CL1-NT3.

Group 12: CL1 was prepared in the same procedure as in Example 1. Then, based on ion exchange method, CL1 (dry weight 10 mg) and NT3 (200 ng) were co-incubated for 1 hour under the condition of 4 degrees on a low speed shaker, and after centrifugation, a precipitate was collected to obtain CL1-NT3.

Group 13: CL1 was prepared in the same procedure as in Example 1. Then, based on ion exchange method, CL1 (dry weight 10 mg) and NT3 (200 ng) were co-incubated for 3 hours under the condition of 4 degrees on a low speed shaker, and after centrifugation, a precipitate was collected to obtain CL1-NT3.

Group 14: CL1 was prepared in the same procedure as in Example 1. Then, based on ion exchange method, CL1 (dry weight 10 mg) and NT3 (200 ng) were co-incubated for 4 hours under the condition of 4 degrees on a low speed shaker, and after centrifugation, a precipitate was collected to obtain CL1-NT3.

Group 15: CL1 was prepared in the same procedure as in Example 1. Then, based on ion exchange method, CL1 (dry weight 10 mg), VEGF and bFGF (the total amount of VEGF and bFGF is 400 ng, and the mass ratio of VEGF to bFGF is 1:1) were co-incubated for 2 hours under the condition of 0 degrees on a low speed shaker, and after centrifugation, a precipitate was collected to obtain CL1-VEGF-bFGF.

Group 16: CL1 was prepared in the same procedure as in Example 1. Then, based on ion exchange method, CL1 (dry weight 10 mg), VEGF and bFGF (the total amount of VEGF and bFGF is 400 ng, and the mass ratio of VEGF to bFGF is 1:1) were co-incubated for 2 hours under the condition of 2 degrees on a low speed shaker, and after centrifugation, a precipitate was collected to obtain CL1-VEGF-bFGF.

Group 17: CL1 was prepared in the same procedure as in Example 1. Then, based on ion exchange method, CL1 (dry weight 10 mg), VEGF and bFGF (the total amount of VEGF and bFGF is 400 ng, and the mass ratio of VEGF to bFGF is 1:1) were co-incubated for 2 hours under the condition of 4 degrees on a low speed shaker, and after centrifugation, a precipitate was collected to obtain CL1-VEGF-bFGF.

Group 18: CL1 was prepared in the same procedure as in Example 1. Then, based on ion exchange method, CL1 (dry weight 10 mg), VEGF and bFGF (the total amount of VEGF and bFGF is 400 ng, and the mass ratio of VEGF to bFGF is 1:1) were co-incubated for 2 hours under the condition of 5 degrees on a low speed shaker, and after centrifugation, a precipitate was collected to obtain CL1-VEGF-bFGF.

Group 19: CL1 was prepared in the same procedure as in Example 1. Then, based on ion exchange method, CL1 (dry weight 10 mg), VEGF and bFGF (the total amount of VEGF and bFGF is 400 ng, and the mass ratio of VEGF to bFGF is 1:1) were co-incubated for 2 hours under the condition of 20 degrees on a low speed shaker, and after centrifugation, a precipitate was collected to obtain CL1-VEGF-bFGF.

Group 20: CL1 was prepared in the same procedure as in Example 1. Then, based on ion exchange method, CL1 (dry weight 10 mg), VEGF and bFGF (the total amount of VEGF and bFGF is 400 ng, and the mass ratio of VEGF to bFGF is 1:1) were co-incubated for 2 hours under the condition of 37 degrees on a low speed shaker, and after centrifugation, a precipitate was collected to obtain CL1-VEGF-bFGF.

Next, the mouse model of spinal cord transaction was established according to the method of Example 7. Mice in the LDH group were filled with CL1 prepared according to the method of Example 1 at the sites of their spinal cord transaction. The other groups of mice were filled with corresponding nano-layered double hydroxide-biological factor materials at the sites of their spinal cord transaction. The volume of the filling materials both are 628 μl. The mice were then routinely cared for. There were 5 mice per group.

1.2 Behavioral Evaluation

The BMS score of the mice was evaluated at the 25th week after surgery to judge the therapeutic effects of the materials. Electrical stimulation was applied to the leg muscles of the mice with a stimulating electrode, and electrical stimulation was received with the receiving electrode at the head end and the tail end of the spinal cord transaction.

1.3 Evaluation of Neural Circuit Reconstruction

At the 25th week after surgery, electrical stimulation was applied to the leg muscles of the mice with a stimulating electrode, and electrical stimulation was received with the receiving electrode at the head end and the tail end of the spinal cord transaction. The electrical signal amplitude values received by the receiving electrode at the head end were measured.

1.4 Data Analysis

The data are analyzed by SPSS 17.0 statistical software. The measurement data are expressed as $\bar{x}\pm S$, and the t test is used. P<0.05 is considered statistically significant.

2 Results

The BMS score and the amplitude value of the 25th week after surgery are shown in Table 1. It shows that the BMS scores of LDH group and group 1-20 are significantly higher than those of the control group, and the difference is statistically significant (P<0.01). Compared with the LDH group, the BMS scores of the groups 1-20 are significantly higher than those of the LDH group, and the difference is statistically significant (P<0.05). Among them, the BMS score of group 8 is significantly higher than the other groups (P<0.05), and the hindlimb motor function is the best. The amplitude values show the same trend as the BMS score, indicating that the reconstruction of the neural circuit in the spinal cord injury area of the mice in each treatment group is significantly promoted, and the nerve conduction function of them is recovered well. Among them, the performance of group 8 is the most prominent, which is significantly better than other groups (P<0.05).

TABLE 1

BMS score and amplitude value of each group ($\bar{x} \pm S$)

| Group | BMS score (point) | Amplitude (uV) |
|---|---|---|
| Control | 0.1 ± 0.1 | 1.8 ± 0.5 |
| LDH | 2.6 ± 0.7** | 27.5 ± 3.8** |
| Group 1 | 5.5 ± 0.7**# | 46.5 ± 5.5**# |
| Group 2 | 5.1 ± 0.9**# | 42.1 ± 5.0**# |
| Group 3 | 4.8 ± 0.8**# | 43.5 ± 4.9**# |
| Group 4 | 4.1 ± 0.7**# | 39.2 ± 3.3**# |
| Group 5 | 4.2 ± 0.6**# | 39.0 ± 4.4**# |
| Group 6 | 3.9 ± 0.4**# | 38.4 ± 4.7**# |
| Group 7 | 4.4 ± 0.5**# | 40.3 ± 5.6**# |
| Group 8 | 6.5 ± 0.8**# | 58.8 ± 6.2**# |
| Group 9 | 4.6 ± 0.6**# | 38.6 ± 3.5**# |
| Group 10 | 4.4 ± 0.5**# | 40.2 ± 3.9**# |
| Group 11 | 4.1 ± 0.5**# | 36.9 ± 3.8**# |
| Group 12 | 4.7 ± 0.7**# | 39.9 ± 4.7**# |
| Group 13 | 4.3 ± 0.8**# | 37.5 ± 4.8**# |
| Group 14 | 4.1 ± 0.7**# | 38.1 ± 4.9**# |
| Group 15 | 3.7 ± 0.6**# | 36.0 ± 4.1**# |
| Group 16 | 4.0 ± 0.5**# | 37.1 ± 4.0**# |
| Group 17 | 3.5 ± 0.4**# | 34.9 ± 3.4**# |
| Group 18 | 3.9 ± 0.7**# | 37.1 ± 3.8**# |
| Group 19 | 4.2 ± 0.7**# | 38.4 ± 3.5**# |
| Group 20 | 3.4 ± 0.6**# | 35.0 ± 3.5**# |

Note:
vs Control,
**P > 0.01.
vs LDH,
P > 0.05.
BMS total score is 9 points.

The materials, methods and uses described herein are presently representative of preferred embodiments. It will be apparent to one skilled in the art that various changes and modifications can be made therein without departing from the spirit and scope thereof. Such changes and modifications are intended to be encompassed by the scope of the following claims.

The invention claimed is:

1. A method of preparing a nano-layered double hydroxide-biological factor combined material comprising:
    a) preparing a nanoparticle suspension by mixing $A(C)_2.6H_2O$ and $B(C)_3.9H_2O$ in water as a solvent followed by adding the mixture to a NaOH solution, followed by centrifuging the nanoparticle suspension at a speed of 5000 rpm to 8500 rpm to obtain a gel; wherein A is a divalent ion selected from the group consisting of Mg, Ca, Cu, and Zn; wherein B is a trivalent ion selected from the group consisting of Al, Fe, and Cr; and wherein C is an anionic acid radical selected from the group consisting of $NO_3^-$ and $CO_3^{2-}$, and
    b) incubating a second mixture of 10 mg of the gel and 200 ng to 2000 ng of a biological factor in a low speed shaker at a temperature of 4° C. for 2 hours, followed by centrifuging the second mixture to obtain a precipitate of the nano-layered double hydroxide-biological factor combined material, wherein the biological factor is neurotrophin-3 (NT3), vascular endothelial growth factor (VEGF) or basic fibroblast growth factor (bFGF).

2. The method of claim 1, wherein the biological factor is NT3.

3. The method of claim 1, wherein A is Mg.

4. The method of claim 1, wherein B is Fe.

5. The method of claim 1, wherein C is $NO_3^-$.

6. The method of claim 1, wherein the biological factor is NT3, and wherein A is Mg, B is Fe, and C is $NO_3^-$.

7. A nano-layered double hydroxide-biological factor combined material prepared by the method of claim 1.

* * * * *